(12) United States Patent
Ziegler

(10) Patent No.: US 8,940,252 B2
(45) Date of Patent: Jan. 27, 2015

(54) RACK APPARATUS FOR A SAMPLE DISTRIBUTION SYSTEM

(75) Inventor: Michael Ziegler, Schwaikheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 579 days.

(21) Appl. No.: 13/129,056

(22) PCT Filed: Nov. 11, 2009

(86) PCT No.: PCT/EP2009/008028
§ 371 (c)(1),
(2), (4) Date: Jul. 29, 2011

(87) PCT Pub. No.: WO2010/054799
PCT Pub. Date: May 20, 2010

(65) Prior Publication Data
US 2011/0274595 A1 Nov. 10, 2011

(30) Foreign Application Priority Data

Nov. 14, 2008 (DE) .......................... 10 2008 058 755

(51) Int. Cl.
*B01L 9/06* (2006.01)
*G01N 35/02* (2006.01)
*G01N 35/04* (2006.01)

(52) U.S. Cl.
CPC ................ *B01L 9/06* (2013.01); *G01N 35/026* (2013.01); *B01L 2200/023* (2013.01); *B01L 2200/025* (2013.01); *G01N 2035/0413* (2013.01)

USPC .......................................................... 422/562

(58) Field of Classification Search
CPC ...... B01L 9/06; B01L 2200/023; B01L 2200/025
USPC .......................... 422/560–562; 211/74, 85.15
See application file for complete search history.

(56) References Cited

U.S. PATENT DOCUMENTS

| | | | | |
|---|---|---|---|---|
| 3,857,606 A | * | 12/1974 | Rodaway | ................ 297/423.37 |
| 5,632,388 A | | 5/1997 | Morrison et al. | |
| 6,193,892 B1 | * | 2/2001 | Krueger et al. | ............... 210/695 |
| 6,752,967 B2 | | 6/2004 | Farina et al. | |
| 7,141,213 B1 | | 11/2006 | Pang et al. | |
| 7,669,721 B2 | | 3/2010 | Kemper et al. | |
| 7,820,115 B2 | | 10/2010 | Zatechka, Jr. et al. | |

(Continued)

FOREIGN PATENT DOCUMENTS

| | | |
|---|---|---|
| DE | 602 13 873 T2 | 9/2007 |
| EP | 1 331 473 A1 | 7/2003 |
| EP | 1 655 609 A1 | 5/2006 |

(Continued)

OTHER PUBLICATIONS

English translation of the International Preliminary Report on Patentability, PCT/IB/338, PCT/IB/373 and PCT/ISA/237. (seven (7) pages).

(Continued)

*Primary Examiner* — Paul Hyun
(74) *Attorney, Agent, or Firm* — Crowell & Moring LLP

(57) ABSTRACT

A rack device for a sample distribution system includes a rack having receptacles for sample carriers and a rack carriage. The rack carriage and the rack can be solidly connected to one another by a latching device that can be released without the use of tools.

13 Claims, 4 Drawing Sheets

(56) References Cited

U.S. PATENT DOCUMENTS

2004/0132068 A1    7/2004  Schubert
2005/0180895 A1*   8/2005  Itoh ............................ 422/104

FOREIGN PATENT DOCUMENTS

| | | | |
|---|---|---|---|
| EP | 1 705 149 | A2 | 9/2006 |
| EP | 1 997 560 | A1 | 12/2008 |
| JP | 2007-303960 | A | 11/2007 |
| WO | WO 2007/087089 | A2 | 8/2007 |

OTHER PUBLICATIONS

German Office Action dated Jun. 19, 2009 with English translation (six (6) pages).

International Search Report dated Mar. 31, 2010 with English translation (six (6) pages).

* cited by examiner

RACK APPARATUS FOR A SAMPLE DISTRIBUTION SYSTEM

This application is a national stage of International Application No. PCT/EP2009/08028, filed Nov. 11, 2009 designating the United States of America. Priority is claimed based on German patent application no. 10 2008 058 755.9 filed Nov. 14, 2008, the entire disclosures of which are herein expressly incorporated by reference.

FIELD OF THE INVENTION

The invention relates to a rack apparatus for a sample distribution system. The invention also relates to a rack and a rack carriage for a rack apparatus.

BACKGROUND AND SUMMARY OF THE INVENTION

A sample distribution system is known, for example, from U.S. Pat. No. 7,141,213 B1. A sample distribution system is used to prepare samples for an analysis or the like. In this process, for example, the samples are divided, centrifuged, mixed with test fluids, etc. In an inlet or loading area sample carriers, especially test tubes, are supplied to the system in so-called racks or sample holders. The supplying occurs, e.g., using drawer-type adjustable pan or drawer elements. In the sample distribution system, the racks can then be slid into specific positions and/or distributed to specific stations. It is also known here to place the rack on a so-called carriage, by which the rack can be driven into the system. Usually several racks next to each other and in rows are arranged on a pan or drawer, wherein the racks are arranged so that they are very closely adjacent to each other.

Providing receiving openings on an underside of the rack is known from U.S. Pat. No. 7,141,213 B1, by means of which the rack can be placed in movement on positioning pins of a carriage.

The object of the present invention is to produce a rack apparatus, wherein a rack can be connected quickly to a rack carriage and the connection can also be loosened without tools even when there is reduced available space.

This object is achieved by a rack apparatus for a sample distribution system comprising a rack with receivers for sample holders and a rack carriage, wherein the rack carriage and the rack are connected tightly to each other by a latching device that can be released without tools. This object is further achieved by a rack and/or a rack carriage for the rack apparatus according to the invention.

In the context of the invention, a tight connection is understood to mean a connection without degrees of freedom, wherein a slight play—e.g., due to manufacturing tolerances—may be present in individual directions. However, preferably there is a connection free from play. The latching device thus allows a fastening of the rack on the rack carriage without degrees of freedom, so the rack apparatus can be manipulated within the sample distribution system in any desired way with high accuracy. A tool-free loosening or connection of the two components is possible using a relative motion.

In one design of the invention, it is provided that the rack apparatus has latching elements complementary to each other arranged on the rack carriage and the rack, and at least one force element for application of a constraining force, whereby a latching connection can be produced or released by a relative motion between the rack carriage and the rack opposite the constraining force. Depending on the design of the latching elements, slight movements can already be adequate for loosening the connection. In one design, the relative motion is a translational motion. In other designs, rotation motions or combination motions are provided for loosening the connection. The required force for loosening preferably lies at 15 to 20 N.

In a further development of the invention, it is provided that the latching elements comprise latching bolts and latching grooves into which the latching bolts can be introduced. In one design, these latching bolts are arranged and dimensioned such that the latching bolts do not extend, or only extend insignificantly, from the rack device in the coupled state.

Preferably it is provided that the latching elements comprise at least one pair of latching bolts, comprising one rigid latching bolt and a movable latching bolt at a distance from it, whereby a distance of the latching bolt against the constraining force of the at least one force element can be changed. In this way, the latching bolts can be constrained into the latching grooves by the force element and held in the latching groove. In an advantageous design, the latching elements comprise at least one latching groove pair complementary to the latching bolt pair with at least two effective surfaces lying over each other, wherein the at least one force element constrains the latching bolt pair on the effective surfaces in a latched connection. The effective surfaces can be arranged so they are turned toward each other or away from each other. To connect, the rack is placed on the movable latching bolt and the latching bolt is slid until the latching groove assigned to the rigid latching bolt can be introduced into this latching bolt. The relative motion necessary for this is a combination motion.

In a further development, on opposite side surfaces of the rack carriage, a pair of latching bolts is provided, whereby the latching bolts are arranged at a distance from each other in the longitudinal direction. In the context of the invention, the longitudinal direction indicates an insertion direction of the rack apparatus into the sample distribution system. The rack and the rack carriage each have essentially rectangular base surfaces depending on their size. In this case, the lateral surfaces that run parallel to the longitudinal direction are designated as side surfaces. Preferably, a pair of latching grooves is provided on each side surface of the rack, in which a latching bolt pair engages for a latched connection. In an arrangement of this type, handling that is especially advantageous ergonomically is possible.

In another design of the invention, it is provided that inserts with elastic spring arms for holding the sample containers are inserted in the receivers. The elastic spring arms permit a good positioning of sample holders, especially of test tubes. Depending on the application, racks with inserts or without inserts, as well as mixed forms, are advantageous. The receivers preferably have a circular cross section. A diameter is, e.g., approx. 13.3 mm or approx. 16.5 mm.

In yet another design of the invention, it is provided that the rack is designed of unbreakable plastic, especially of polycarbonate, e.g., Lexan (CAS#25971-63-5).

In yet another design of the invention, it is provided that the rack is designed of an autoclavable plastic, especially of polycarbonate, e.g., Lexan (CAS#25971-63-5).

In a further development of the invention, it is provided that the rack is composed of an upper part and a lower part that is tightly connected to the upper part, especially welded or glued. Because of this, simple manufacturing is possible, for example using injection molding.

Preferably, it is provided that the lower part and the upper part have receivers arranged so they match each other for sample carriers, whereby the receivers of the lower part are designed so that they are narrowed conically. Because of the conical narrowing, test tubes with different diameters have to be held. The narrowing can occur continuously or in steps. The receivers preferably have a circular cross section.

In a further design of the invention, it is provided that the rack carriage is at least partially designed of a material that is magnetic and/or can be magnetized. In this way, the rack carriage can be coupled in a simple manner with different stations of the sample distribution system. For example, the rack carriage can be manufactured cost-effectively as a bent stamped part. In other designs, the rack carriage is made of a plastic.

In yet another design of the invention, it is provided that the rack carriage has coupling elements, especially positioning pins, for coupling with the sample distribution system. The coupling elements can be designed optionally. In their design, the coupling elements comprise a coding for recognition of a rack type.

Other advantages of the invention can be seen from the description below of exemplary embodiments of the invention, which are represented schematically in the drawings. For the same or similar components, uniform reference numbers are used in the drawings. Characteristics that are described or represented as part of an exemplary embodiment can also be used in a different exemplary embodiment in order to obtain an additional embodiment of the invention.

DETAILED DESCRIPTION OF THE DRAWINGS

Figure 1:
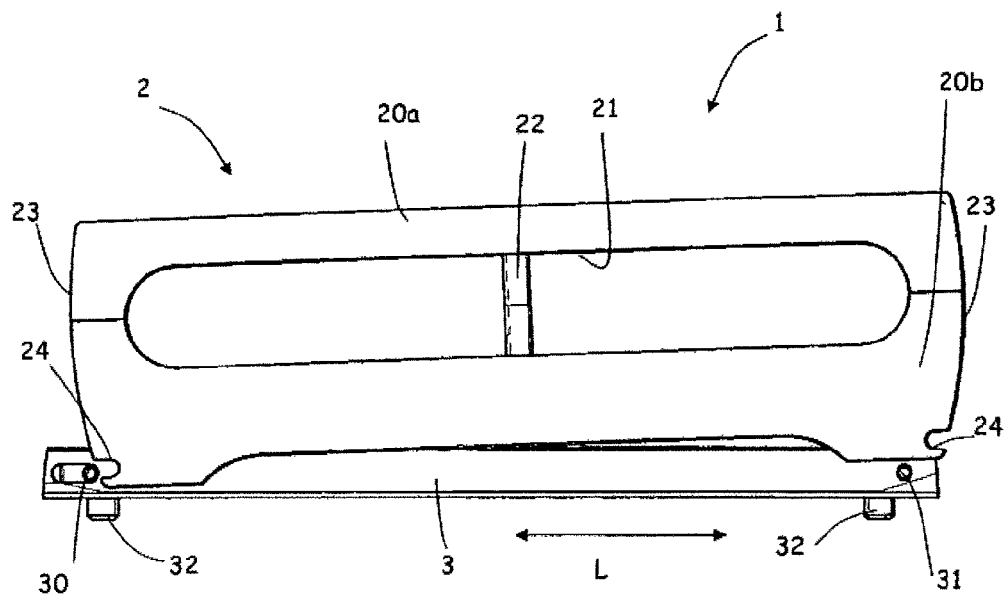
FIG. 1: shows a schematic side view of a rack apparatus according to the invention during installation of a rack on a rack carriage.

FIG. 1 schematically shows a rack apparatus 1 according to the invention, comprising a rack 2 and a rack carriage 3, which according to the invention can be connected tightly to each other by a latching device that can be released without tools.

In the exemplary embodiment shown, the rack 2 is made of two plastic parts, with an upper part 20a and a lower part 20b, which are tightly connected to each other, e.g., glued and/or welded. The upper part 20a and the lower part 20b are connected to each other in such a way that a gripping recess 21 remains for simple handling of the rack 2. To increase the stability of the rack 2, ribs 22 are provided between the upper part 20a and the lower part 20b.

For connection with the rack carriage 3, latching grooves 24 are provided on face sides 23 of the rack 2, which latching grooves 24 are each open in the direction of face surfaces 23 in the exemplary embodiment shown. For connection with the rack carriage 3, the latching grooves 24 are placed on latching bolts 30, 31 of the rack carriage. In the exemplary embodiment shown, the latching bolts 30, 31 extend from one outer side of the rack carriage 3. The associated rack 2 can be placed on the rack carriage 3 in such a way that inner sides of the lower part 20b lie opposite the outer sides of the rack carriage 3. The latching grooves 24 and/or the latching bolts 30, 31 are spaced in pairs in longitudinal direction L of the rack apparatus 1. In this case, longitudinal direction L indicates a direction in which that rack apparatus 1 can be installed in a sample distribution system that is not shown. Because of the arrangement of the latching bolts 30, 31, on these side surfaces an especially simple handling is implemented. However, designs are also contemplated in which latching bolts 30, 31 and the associated latching grooves 24 are provided on face surfaces of the rack apparatus 1.

In order to permit a placement of the latching grooves 24 on the latching bolts 30, 31, the latching bolt 30 is mounted so it is movable. In other designs, the latching bolts 30 themselves are elastically deformable so the force element is designed to form one part with the latching bolt.

For connection of the rack 2 with the latching carriage 3, first, as shown schematically in FIG. 1, the rack 2 is guided with its latching groove 24 on the movable latching bolt 30. The movable latching bolt 30 can be slid in longitudinal direction L with the rack 2 placed on it until an installation of the latching groove 24 onto the rigidly mounted latching bolt 31 is possible. In order to secure the latched connection, the latching bolt 30 is held in the latched position shown in FIG. 1 by means of a force element, especially by means of a spring. Producing or releasing the latched connection is thus only possible by overcoming the constraining force applied by the spring.

The rack carriage 3 has coupling elements 32, which are designed as positioning pins in the exemplary embodiment shown. With these coupling elements 32, the rack carriage 3 can be connected with corresponding elements of the sample distribution that is not shown. The rack carriage 3 is preferably made of a material that is magnetic and/or can be magnetized so that a coupling of the rack carriage 3 with the sample distribution system is also possible using magnetic force.

Figure 2:
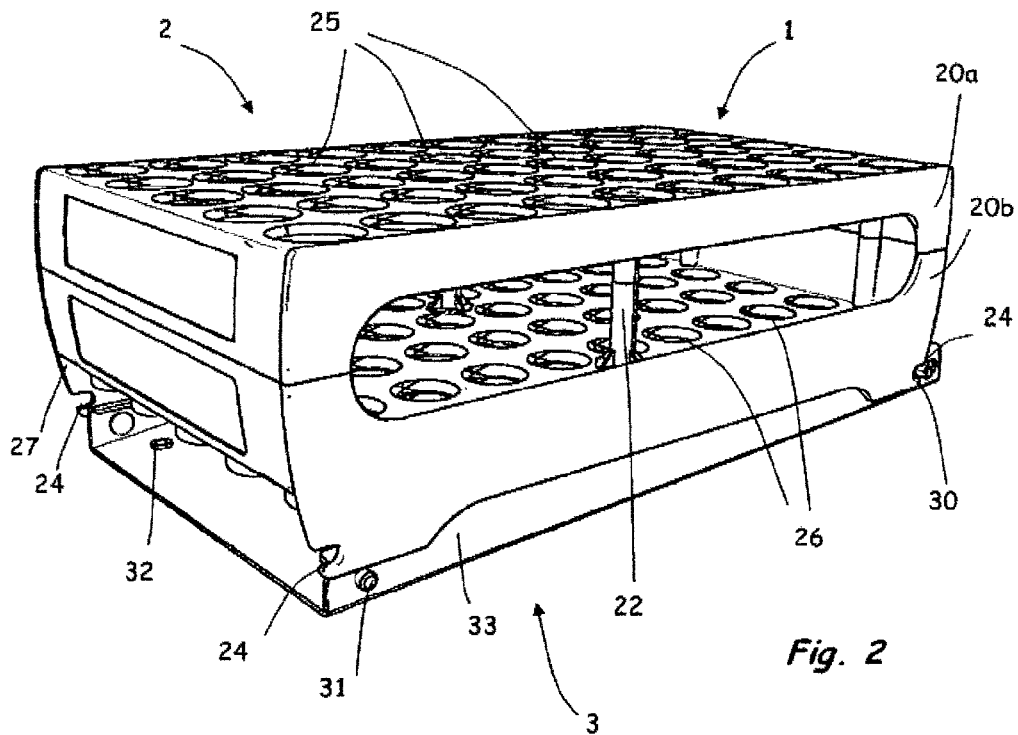
FIG. 2: shows the rack apparatus according to FIG. 1 in a perspective view.

FIG. 2 schematically shows the rack apparatus 1 according to FIG. 1 in a perspective view from the other side. As can be seen from FIG. 2, the upper part 20a and the lower part 20b each have receivers 25, 26, in which sample holders (not shown in FIG. 2), especially test tubes, can be inserted. As can also be seen from FIG. 2, the rack carriage 3 is essentially designed as a U-shaped part with a rectangular base surface. The rack 2 can be placed on the rack carriage 3 in such a way that the inner surfaces 27 of the lower part 20b can come to rest on the outer sides 33 of the flanks of the rack carriage 3.

Figure 3:
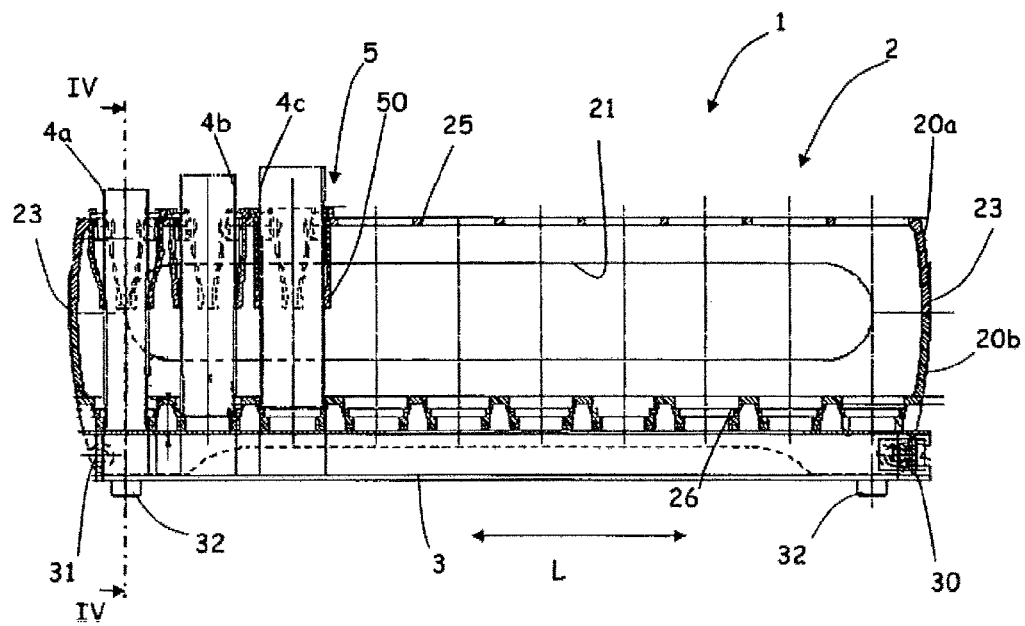
FIG. 3: shows the rack apparatus according to FIG. 1 in a cross-section side view.

FIG. 3 schematically shows a cross section side view of a rack apparatus according to FIG. 1, with three sample holders 4a, 4b and 4c held in it. In the exemplary embodiment shown, inserts 5 with spring arms 50 are inserted in the receivers 25 of the upper part 20a, by which the sample holders 4a, 4b, 4c are securely held in the receivers 25. As can also be seen from FIG. 3, the receivers 26 in the lower part 20b are conical in design, whereby the diameter of the receivers 26 is designed so that it narrows in steps toward the bottom. Because of this, a receiving of sample holders 4a, 4b, 4c with different diameters, as shown schematically in FIG. 3, is improved.

Figure 4:
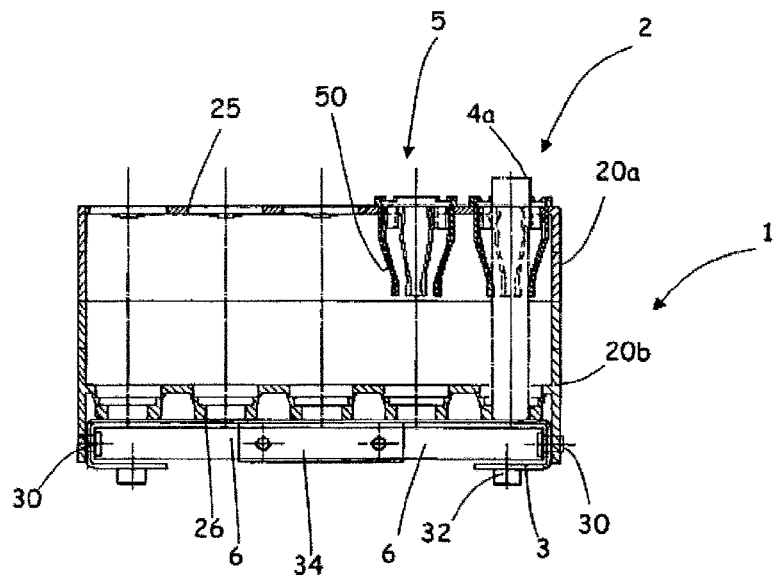
FIG. 4: shows the rack apparatus according to FIG. 3 in a cross section front view.

FIG. 4 schematically shows a cross section view of the rack apparatus 1 along line IV-IV according to FIG. 3. As can be recognized in FIG. 4, the rack carriage 3 has a fastening device 34. On the fastening device 34, force elements designed as leaf springs 6 are fastened, by which the movable latching bolt 30 can be constrained in the latching position.

In the embodiment of a rack apparatus 1, according to FIGS. 1 to 4, fifty receivers 25 and/or 26 are provided, which are arranged ordered in rows and columns, wherein five columns are provided in which ten receivers 25, 26 each are formed. However, designs with a number of columns and/or number of rows deviating from this are also contemplated. Usually embodiments are preferred that have five columns, wherein four, five, ten, fifteen or even thirty rows can be provided. However, optional other designs are of course also contemplated.

Figure 5:
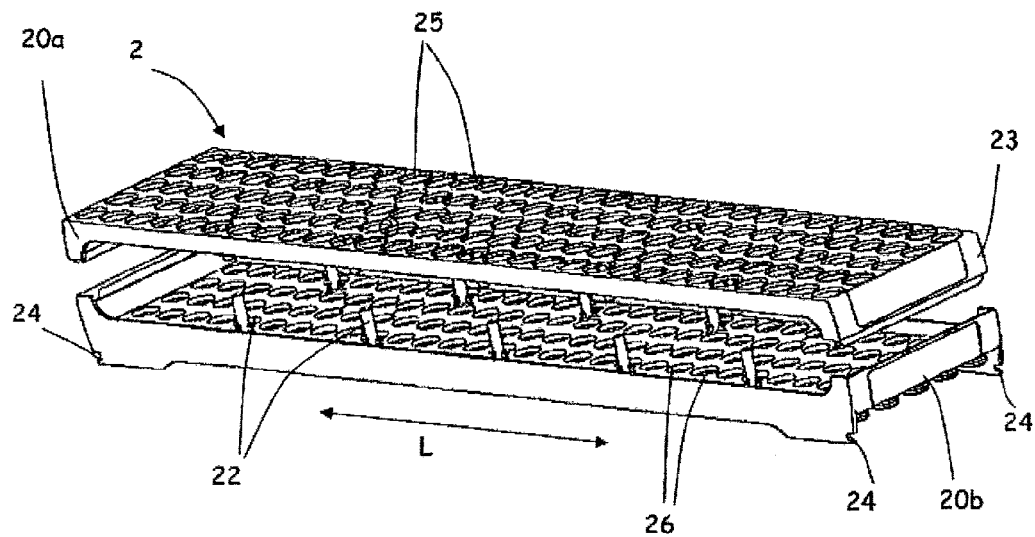
FIG. 5: shows a rack according to the invention for a rack apparatus similar to FIG. 1 in an exploded view.

FIG. 5 schematically shows a rack 2 according to a second exemplary embodiment of the invention, wherein receivers 25, 26 are provided in thirty rows with five receivers 25, 26 in each. The rack apparatus 1 according to FIG. 5 corresponds essentially to the rack apparatus 1 according to FIGS. 1 to 4. For similar components, uniform reference numbers are used and a detailed description of these components will be dispensed with. Because of the increased length in longitudinal direction L, the number of connecting ribs 22 between the upper part 20*a* and the lower part 20*b* is increased to improve the stability.

Figure 6:
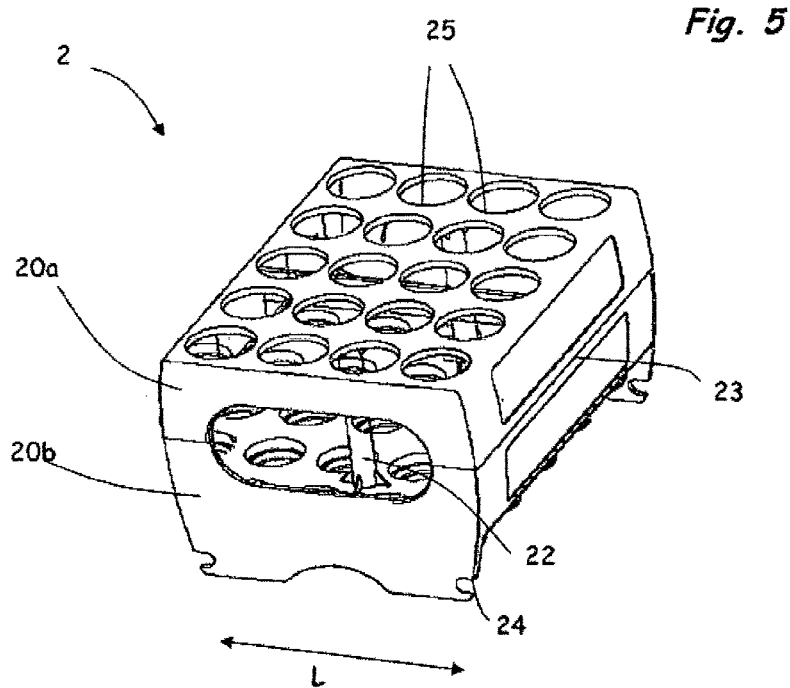
FIG. 6: shows another design of a rack for a rack apparatus according to the invention.

FIG. 6 schematically shows, in perspective view, another embodiment of a rack 2, wherein only four rows of receivers 25, 26 are provided.

Figure 7:
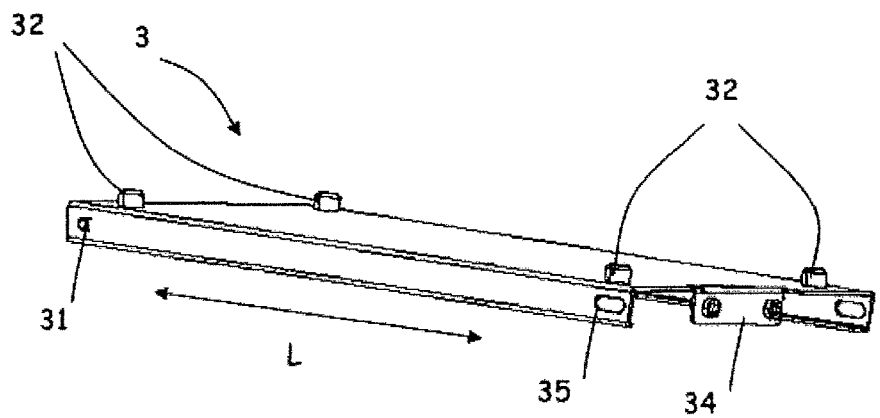
FIG. 7: shows a rack carriage for a rack apparatus according to the invention in a perspective view
Figure 8:
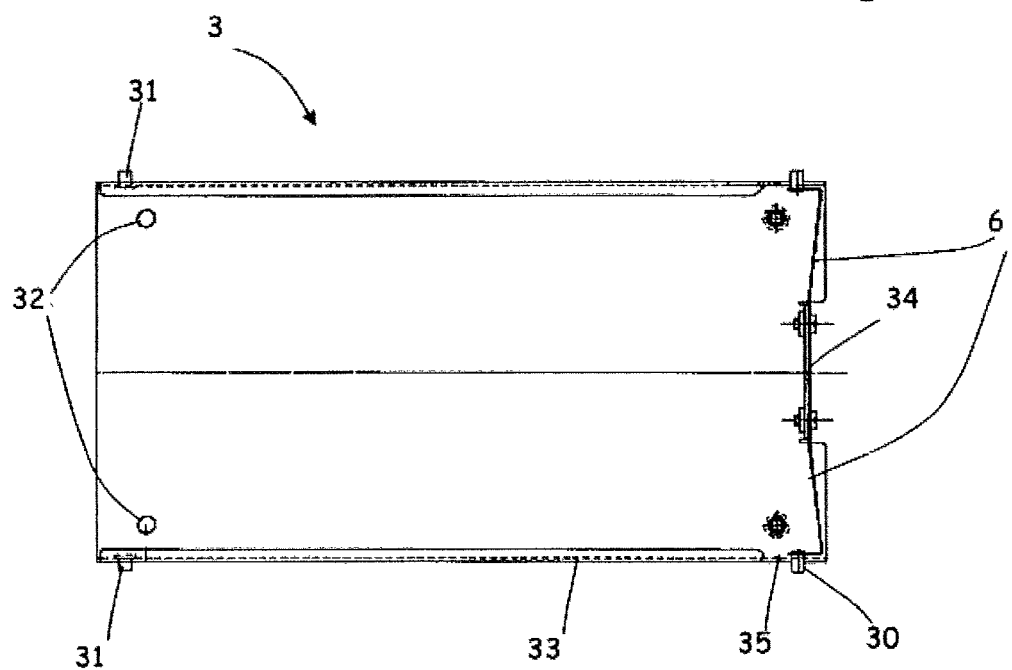
FIG. 8: shows a top view of the rack carriage according to FIG. 7 with leaf springs mounted on it.

FIGS. 7 and 8 schematically show a rack carriage 3 for a rack apparatus according to the invention, wherein in FIG. 7 the leaf springs 6 are not shown for the sake of clarity. As already described, the rack carriage 3 has a fastening device 34, on which leaf springs 6 are mounted in such a way that latching bolts 30 connected with the leaf springs 6 are guided into a slot 35 provided in one of the side flanks 33 of the rack carriage 3.

Because of the latching device according to the invention, it is possible to connect a rack 2 with the associated rack carriage 3 in a simple manner and without tools. In this case, several rack carriages 3 and/or rack apparatuses 1 can be arranged close to each other, next to each other and in rows, in a small installation space, e.g., in a drawer or an inlet area of a sample distribution system without impeding the handling of the rack apparatus 1 in producing or releasing the latched connection.

The invention claimed is:

1. A rack apparatus for a sample distribution system, comprising:
   a rack with receivers for sample holders;
   a rack carriage; and
   a latching device by which the rack carriage and the rack are tightly connectable and releasable with each other without use of tools,
   wherein the latching device comprises
      latching elements complementary to each other mounted on the rack carriage and the rack and
      a force element for applying a constraining force, wherein
         a latched connection is made or released via a relative motion between the rack carriage and the rack, the relative motion being a combination of a translational motion opposite the constraining force and a rotational motion, and
      the latching elements comprise
         at least one latching bolt pair formed by a rigid latching bolt and a movable latching bolt, the moveable latching bolt being arranged at a distance from the rigid latching bolt, and
         latching grooves, the latching bolts being introduced into the latching grooves forming the latched connection, whereby the distance between the latching bolt pair is changeable opposite the constraining force of the force element.

2. The rack apparatus according to claim 1, wherein:
   the latching grooves comprise at least one latching groove pair complementary to the latching bolt pair, the latching groove pair having at least two opposite effective surfaces, whereby in the latched connection, the force element constrains the latching bolt pair on the at least two opposite effective surfaces.

3. The rack apparatus according to claim 2, wherein one latching bolt pair is provided on each of opposite side surfaces of the rack carriage, the latching bolts of each latching bolt pair being arranged at a distance from each other in a longitudinal direction.

4. The rack apparatus according to claim 1, wherein one latching bolt pair is provided on each of opposite side surfaces of the rack carriage, the latching bolts of each latching bolt pair being arranged at a distance from each other in a longitudinal direction.

5. The rack apparatus according to claim 4, wherein on each side surface of the rack, a latching groove pair is provided in which a latching bolt pair engages for forming the latched connection.

6. The rack apparatus according to claim 3, wherein on each side surface of the rack, a latching groove pair is provided in which a latching bolt pair engages for forming the latched connection.

7. The rack apparatus according to claim 1, further comprising:
   inserts having elastic spring arms, the inserts being inserted in the receivers of the rack for holding the sample holders.

8. The rack apparatus according to claim 1, wherein the rack is made of polycarbonate.

9. The rack apparatus according to claim 1, wherein the rack comprises an upper part and a lower part, the lower part being tightly connected to the upper part.

10. The rack apparatus according to claim 9, wherein the lower part and the upper part have receivers arranged to match one another in order to receive the sample holders, the rack apparatus further comprising inserts arranged in the receivers of the lower part, the inserts being narrowed conically.

11. The rack apparatus according to claim 1, wherein the rack carriage is made of at least one of a partially magnetic and magnetizable material.

12. The rack apparatus according to claim 1, wherein the rack carriage comprises coupling elements on an underside, the coupling elements being operatively configured for coupling with the sample distribution system.

13. The rack apparatus according to claim 12, wherein the coupling elements are positioning pins.

\* \* \* \* \*